United States Patent [19]
Chu et al.

[11] Patent Number: 5,503,984
[45] Date of Patent: Apr. 2, 1996

[54] HYBRIDOMA PRODUCING MONOCLONAL ANTIBODY F4 WHICH SPECIFICALLY BINDS TO MULTIDRUG RESISTANT P-GLYCOPROTEIN AND ASSAYS FOR DETECTION OF P-GLYCOPROTEIN

[75] Inventors: Tsann M. Chu, Williamsville; Elzbieta Kawinski, Orchard Park, both of N.Y.; Tsung-hsing Lin, Chapel Hill, N.C.

[73] Assignee: Health Research, Inc., Buffalo, N.Y.

[21] Appl. No.: 47,117

[22] Filed: Apr. 13, 1993

[51] Int. Cl.$^6$ .......................... G01N 33/53; C07K 16/30; C12N 5/20
[52] U.S. Cl. ................................. 435/7.23; 435/240.27; 435/172.2; 435/70.21; 530/388.8; 530/388.85; 530/388.7
[58] Field of Search .......................... 530/387.7, 388.22, 530/388.85; 435/240.27, 172.2, 70.21, 7.23, 7.1

[56] References Cited

U.S. PATENT DOCUMENTS 4,837,306  6/1989  Ling et al. .

FOREIGN PATENT DOCUMENTS 1263324  11/1989  Canada .

OTHER PUBLICATIONS

Juranka et al., "P–glycoprotein: Multidrug–Resistance and a Superfamily of Membrane–Associated Transport Proteins", The FASEB Journal, vol. 3, pp. 2583–2592, (1989).
Bell et al., "Multidrug Resistance: A Novel Class of Membrane–Associated Transport Proteins is Identified", Cancer Investigation, 9(5), 563–569, (1991).
Pastan et al., "Molecular Manipulations of the Multidrug Transporter: A New Role for Transgenic Mice", The FASEB Journal, vol. 5, pp. 2523–2528, (1991).
Roninson et al., "Isolation of Human mdr DNA Sequences Amplified in Multidrug–resistant KB Carcinoma Cells", Proc. Natl. Acad. Sci., vol. 83, pp. 4538–4542, (1986).
Kartner et al., "Detection of P–glycoprotein in Multidrug–resistant Cell Lines by Monoclonal Antibodies", Nature, vol. 316, pp. 820–823, (1985).
Lathan et al., "Immunological Detection of Chinese Hamster Ovary Cells Expressing a Multidrug Resistance Phenotype", Cancer Research 45, pp. 5064–5069, (1985).
Hamada et al., "Functional Role for the 170– to 180–kDa Glycoprotein Specific to Drug–Resistant Tumor Cells as Revealed by Monoclonal Antibodies", Proc. Natl. Acad. Sci., vol. 83, pp. 7785–7789, (1986).
Scheper et al., "Monoclonal Antibody JSB–1 Detects a Highly Conserved Epitope on the P–Glycoprotein Associated with Multi–Drug–Resistance", Int. J. Cancer: 42, pp. 389–394, (1988).
Meyers et al., "Characterization of Monoclonal Antibodies Recognizing a Mr 180,000 P–Glycoprotein: Differential Expression of the Mr 180,000 and Mr 170,000 P–Glycoproteins in Multidrug–resistant Human Tumor Cells", Cancer Research 49, pp. 3209–3214, (1989).

Chabner et al., "Multidrug Resistance: P–glycoprotein and Its Allies—The Elusive Foes", Journal of the National Cancer Institute, vol. 81, No. 12, (1989).
Dalton et al., "Does P–Glycoprotein Predict Response to Chemotherapy, And If So, Is There A Reliable Way to Detect it?", Journal of the National Cancer Institute, vol. 83, No. 2, (1991).
Beck, "Do Anti–P–Glycoprotein Antibodies Have a Future in the Circumvention of Multidrug Resistance?" Journal of the National Cancer Institute, vol. 83, No. 19, pp. 1364–1366, (1991).
Rogan et al., "Reversal of Adriamycin Resistance by Verapamil in Human Ovarian Cancer", Science, vol. 224, pp. 994–996, (1984).
Cowan et al., "Similar Biochemical Changes Associated with Multidrug Resistance in Human Breast Cancer Cells and Carcinogen–induced Resistance to Xenobiotics in Rats", Proc. Natl. Acad. Sci. USA, vol. 83, pp. 9328–9332, (1986).
Akiyama et al., "Isolation and Genetic Characterization of Human KB Cell Lines Resistant to Multiple Drugs", Somatic Cell and Molecular Genetics, vol. 11, No. 2, pp. 117–126, (1985).
Biedler et al., "Drug Resistance in Chinese Hamster Lung and Mouse Tumor Cells", Cancer Treatment Reports, vol. 67, No. 10, pp. 859–867, (1983).
Godling, "Antibody Production by Hybridomas", Journal of Immunological Methods, 39, pp. 285–308, (1980).
Papsidero et al., "Monoclonal Antibodies (F36/22 and M7/105) to Human Breast Carcinoma", Cancer Research 43, pp. 1741–1747, (1983).

(List continued on next page.)

Primary Examiner—Paula K. Hutzell
Attorney, Agent, or Firm—Michael L. Dunn

[57] ABSTRACT

A unique monoclonal antibody against P-glycoprotein. The monoclonal antibody is different than those previously described and has the surprising property of reacting to a soluble form of P-glycoprotein. The invention further includes a novel hybridoma cell line which produces the antibody. A preferred embodiment of the novel antibody has been designated F4 which is believed to react at or near an extracellular transmembrane loop of P-glycoprotein selected from the group consisting of the third and sixth extracellular loops. The invention further comprises a method for detecting the presence of P-glycoprotein comprising reacting a specimen containing P-glycoprotein with the novel monoclonal antibody and detecting the reaction to show that P-glycoprotein is present. The invention, in a preferred embodiment, comprises detecting the presence of drug resistant carcinoma cells, in the absence of biopsy, comprising removing extracellular fluids from a patient for use as a specimen, and determining the presence of P-glycoprotein in the specimen by reacting the specimen with the novel monoclonal antibody to show that P-glycoprotein is present as an indicator of drug resistance. The extracellular fluid may be any suitable fluid which could contain P-glycoprotein as an indicator of drug resistance. Such fluids may for example be plasma, lymph excretions, and especially ascites taken from the area of a tumor site.

6 Claims, 7 Drawing Sheets

OTHER PUBLICATIONS

Riordan et al., "Purification of P–Glycoprotein from Plasma Membrane Vesicles of Chinese Hamster Ovary Cell Mutants with Reduced Colchicine Permeability", The Journal of Biological Chemistry, vol. 254, No. 24, pp. 12701–12705, (1979).

Peterson, "A Simplification of the Protein Assay Method of Lowry et al. which is More Generally Applicable", Analytical Biochemistry, 83, pp. 346–356, (1977).

Sonoda et al., "Studies of $^{125}$I Trace Labeling of Immunoglobulin G by Chloramine–T", Immunochemistry, vol. 7, pp. 885–898, (1970).

Gerhard et al., "Applications of Monoclonal Antibodies in Virology", In: Weir, D. M. (ed.), Handbook of Experimental Immunology, vol. 4, pp. 115.1–115.13, London: Blackwell Sci. Publ, (1986).

Chu et al., "Prostate–Specific Antigenic Domain of Human Prostate Specific Antigen Identified with Monoclonal Antibodies", The Journal of Urology, vol. 141, pp. 152–156, (1989).

Papsidero et al., "Immunoaffinity Isolation of Ductal Carcinoma Antigen Using Monoclonal Antibody F36/22", Molecular Immunology, vol. 21, No. 10, pp. 955–960, (1984).

Weiss et al., "Effects of Cytoskeletal Perturbation on the Sensitivity of Ehrlich Ascites Tumor Cell Surface Membranes to Mechanical Trauma", Invasion Metastasis, vol. 11, pp. 93–101, (1991).

Towbin et al., "Electrophoretic Transfer of Proteins from Polyacrylamide Gels to Nitrocellulose Sheets: Procedure and Some Applications", Proc. Natl. Acad. Sci., vol. 76, No. 9, pp. 4350–4354, (1979).

Laemmli, "Cleavage of Structural Proteins During the Assembly of the Head of Bacteriophage T4", Nature, vol. 227, pp. 680–685, (1970).

Croghan et al., "Tissue Distribution of an Epithelial and Tumor–associated Antigen Recognized by Monoclonal Antibody F36/22", Cancer Research 43, pp. 4980–4988, (1983).

Willingham et al., "Immunocytochemical Localization of P170 at the Plasma Membrane of Multidrug–resistant Human Cells", The Journal of Histochemistry and Cytochemistry, vol. 35, No. 12, pp. 1451–1456, (1987).

Georges et al., "Detection of P–glycoprotein Isoforms by Gene–specific Monoclonal Antibodies", Proc. Natl. Acad. Sci., vol. 87, pp. 152–156, (1990).

Danks et al., "Monoclonal Antibodies to Glycoproteins of Vinca Alkaloid–resistant Human Leukemic Cells", Cancer Research 45, pp. 3220–3224, (1985).

Chen et al., "Internal Duplication and Homology with Bacterial Transport Proteins in the mdrl (P–Glycoprotein) Gene from Multidrug–Resistant Human Cells", Cell, vol. 47, 381–389, (1986).

Pauletti et al., "Application of a Modified Computer Algorithm in Determining Potential Antigenic Determinants Associated with the AIDS Virus Glycoprotein", Analytical Biochemistry 151, pp. 540–546, (1985).

Thiebaut et al., "Cellular Localization of the Multidrug–resistant gene product P–glycoprotein in Norman Human Tissues", Proc. Natl. Acad. Sci., vol. 84, pp. 7735–7738, (1987).

Georges et al. J. Biol. Chem 268(3):1792–1798 Jan. 25, 1993.

HYBRIDOMA PRODUCING MONOCLONAL ANTIBODY F4 WHICH SPECIFICALLY BINDS TO MULTIDRUG RESISTANT P-GLYCOPROTEIN AND ASSAYS FOR DETECTION OF P-GLYCOPROTEIN

BACKGROUND OF THE INVENTION

This invention relates to a monoclonal antibody against P-glycoprotein and its use in detecting drug resistant carcinoma.

Multidrug resistance in human cancer is a unique phenomenon and is commonly associated with an overexpression of the human multidrug resistant gene mdrl, which encodes an energy-dependent Mr 170,000 transmembrane protein, also known as P-glycoprotein. One biological function of P-glycoprotein is to transport some chemotherapeutic agents out of cancer cells, thereby conferring a drug resistant phenotype to cancer cells expressing P-glycoprotein. The recognition of the importance of a complexed drug resistant phenotype of broad spectrum in human cancer has prompted an extensive investigation of this phenomenon in vitro using drug resistant cell lines (Juranka, P. F. et al., P-Glycoprotein: multidrug-resistance and a super family of membrane-associated transport protein. *FASEB J.* 3: 2583–2592, 1989; Pastan, I. et al., Molecular manipulation of the multidrug transporter: a new role for transgenic mice. *FASEB J. 5:* 2523–2528, 1991; Gros, P. et al., Multidrug resistance: A novel class of membrane-associated transport protein is identified. *Cancer Invest.* 9: 563–569, 1991; Roninson, I. B. et al., Isolation of human mdr DNA sequences amplified in multidrug-resistant KB carcinoma cells. *Proc. Natl. Acad. Sci. USA* 83: 4538–4542, 1986; Ling, V. et al., U.S. Pat. No. 4,837,306 and Canadian Patent 1,263,324.) All patents and other documents cited herein are incorporated herein by reference.

Immunological and molecular biology techniques have permitted the identification, isolation, and characterization of the mdrl gene, and its encoded P-glycoprotein. Recent study has revealed that P-glycoprotein represents a member of a large family of homologous membrane associated transport proteins, which are implicated in multidrug resistance and other diseases. Biochemically, P-glycoprotein is found in the plasma membrane enriched fraction, is glycosylated, exhibits ATPase activity, binds photoactivatable ATP, and drug analogs. The prototype P-glycoprotein is consisted of twelve transmembrane domains capable of forming six transmembrane loops, a cluster of putative N-linked glycosylation sites located between the first and second proposed transmembrane domain, and two predicted cytoplasmic ATP binding sites. Additionally, peptide portion of P-glycoprotein is composed of two highly symmetrical halves.

From an immunochemical point of view, this seemingly complex and large glycoprotein structure would represent at least a dozen of distinct antigenic determinants. Yet, only a handful of McAb directed against human P-glycoprotein have been generated (Kartner, N. et al., Detection of P-glycoprotein in multidrug-resistant cell lines by monoclonal antibodies. *Nature* (Lond.) 316: 820–823, 1985; Lathan, B. et al., Immunological detection of Chinese hamster ovary cells expressing a multidrug resistance phenotype. *Cancer Res.* 45: 45064–5069, 1985; Hamada, H. et al., Functional role for the 170- to 180-kDa glycoprotein specific to drug-resistant tumor cell as revealed by monoclonal antibodies. *Proc. Natl. Acad. Sci. USA* 83: 7785–7789, 1986; Scheper, R. J. et al., Monoclonal antibody JSB-1 detects a highly conserved epitope on the P-glycoprotein associated with multi-drug resistance. *Int. J. Cancer* 42: 389–394, 1988; Meyers, M. B., et al., Characterization of monoclonal antibodies recognizing a Mr 180,000 P-glycoprotein: Differential expression of the Mr 180,000 and Mr 170,000 P-glycoproteins in multi-drug resistant human tumor cells. *Cancer Res.* 49: 3209–3214, 1989), in spite of the importance of multidrug resistance in pharmacology and therapy of cancer (Chabner, B. A. et al., Multidrug resistance: P-glycoprotein and its allies-the elusive foes. *J. Natl. Cancer Inst.* 81: 910–913, 1989; Dalton et al., Does P-glycoprotein predict response to chemotherapy, and if so, is there a reliable way to detect it? *J. Natl. Cancer. Inst.* 83: 80–84, 1991; Beck, W. T., Do anti-P-glycoprotein antibodies have a future in the circumvention of multidrug resistance? *J. Natl. Cancer Inst.* 83: 1364–1366, 1991). There have further been problems associated with the use of P-glycoprotein in detecting drug resistant cancer cells since biopsy and cell lysing and/or other complicated preparation has been required often taking up to one weeks time to complete an analysis and as long as 2–5 days, even when the procedures are rushed, e.g. by twenty-four hour staffing of the laboratory doing the test.

BRIEF DESCRIPTION OF THE INVENTION

In accordance with the present invention we have developed and discovered a unique monoclonal antibody against P-glycoprotein. The monoclonal antibody is different than those previously described and has the surprising property of reacting to a soluble form of P-glycoprotein. "Soluble P-glycoprotein" as used herein is intended to include forms of P-glycoprotein which are soluble in aqueous systems including fractions or sections of P-glycoprotein which are soluble and contain P-glycoprotein specific epitopes.

A preferred embodiment of the novel antibody has been designated F4. The invention also includes a hybridoma cell line, also designated F4, which produces the F4 antibody. In another preferred embodiment, the antibody of the invention reacts at or near (collectively referred to as proximate) an extracellular transmembrane loop of P-glycoprotein selected from the group consisting of the third and sixth extracellular loops.

The invention further comprises a method for detecting the presence of P-glycoprotein comprising reacting a specimen containing P-glycoprotein with the novel monoclonal antibody and detecting the reaction to show that P-glycoprotein is present.

The invention, in a preferred embodiment, comprises detecting the presence of drug resistant carcinoma cells, in the absence of biopsy, comprising removing extracellular fluids from a patient for use as a specimen, and determining the presence of P-glycoprotein in the specimen by reacting the specimen with the the novel monoclonal antibody to show that P-glycoprotein is present as an indicator of drug resistance.

The extracellular fluid may be any suitable fluid which could contain P-glycoprotein as an indicator of drug resistance. Such fluids may for example be plasma, lymph excretions, and especially ascites taken from the area of a tumor site.

In accordance with the methods of the invention, the reaction between the monoclonal antibody and P-glycoprotein may be detected using any suitable procedure, e.g. a procedure selected from chemiluminescence, radioimmunoassay, immunofluorescence, colorometric analysis or spectrophotometry.

DETAILED DESCRIPTION OF THE INVENTION

In accordance with a preferred embodiment of the invention, we have derived a new McAb, designated F4, reacting with a cell surface determinant of drug resistant tumor cell lines, which turns out to be an extracellular site of P-glycoprotein. McAb F4 is different from the commonly known McAb, such as C219, JSB-1, and MRK16, which recognize an intracellular and extracellular epitope of P-glycoprotein, respectively.

Using viable adriamycin resistant human ovarian carcinoma cells $2780^{AD}$ and colchicine resistant human oral epidermoid carcinoma cells KB-24 as the immunogen in primary and subsequent i.p. immunizations, followed by i.v. boostings with crude plasma membranes of $2870^{AD}$, KB-24, Chinese hamster lung cells resistant to vincristine DC-3F/VCRd-5L, and resistant to daunorubicin DC-3F/DMXX, we have generated a new murine monoclonal antibody (McAb), designated F4, of IgG1 isotype. McAb F4 reacted strongly with a cell surface epitope of drug resistant cells and insignificantly with their drug sensitive counterparts. Cell surface localization of F4 epitope was determined by flow cytometry and laser scanning confocal imaging system. Results obtained from immunoprecipitation and immunoblot analyses using F4 and P-glycoprotein specific McAb C219 demonstrated the reactivity of P-glycoprotein with F4. These results along with those obtained from competitive binding inhibition, chemical modification, and enzyme hydrolysis, revealed that McAb F4 detects an extracellular epitope of P-glycoprotein, and is different from other McAb directed against P-glycoprotein, e.g. C219, MRK16, JSB-1, HYB-241, C494, C32, 265/F4, and 32G7. Deduced from the putative structure of mdr1 protein and its orientation in cell membrane, it is proposed that F4 epitope is localized in or near the third or 6th extracellular transmembrane loop of P-glycoprotein. F4 has been found to be able to detect a soluble P-glycoprotein in body fluids, especially ascites.

The hybridoma cell line, designated F4, which produces this novel monoclonal antibody was deposited with the ATCC 12301 Parklawn Drive, Rockville, Md., on Apr. 13, 1993 having deposit number HB11325in accordance with the patent requirements of the United States and the Budapest Treaty on the international recognition of the deposit of microorganisms for the purposes of patent procedure.

Certain abbreviations used repeatedly throughout the specification are as follows: McAb, monoclonal antibody; ELISA, enzyme linked immunosorbent assay; RIA, radioimmunoassay; PBS, phosphate-buffered saline; BSA, bovine serum albumin; SDS, sodium dodecyl sulfate; PAGE, polyacrylamide gel electrophoresis; RPMI, Roswell Park Memorial Institute, Buffalo, N.Y.; I.P., interperitoneal; i.v., intravenous; ATCC, American Type Culture Collection.

Materials and Methods

Cell Line and Culture. Human ovarian carcinoma cell line A2780 and breast carcinoma cell line MCF-7 sensitive in vitro to adriamycin, and their adriamycin resistant variants $2780^{AD}$ and MCF-$7^{AD}$ were maintained in RPMI 1640 and appropriate media (Rogan, A. M. et al., Reversal of adriamycin resistance by verapamil in human ovarian cancer. *Science* 224: 934–996, 1984; Cowan, K. H. et al., Similar biochemical changes associated with multidrug resistance to xenobiotics in rats. *Proc. Natl. Acad. Sci.* USA 83: 9328–9332, 1986). Human KB oral epidermoid carcinoma cell line KB-3-1 sensitive in vitro to colchicine, and its colchicine resistant sublines, KB-5, KB-10, KB-100, and KB-24, were maintained in minimum essential medium (Akiyama, S. et al., Isolation and genetic characterization of human KB cell lines resistant to multiple drugs. *Somatic Cell Mol. Genet.* 11: 117–126, 1985). Chinese hamster lung cells DC-3F and its vincristine resistant subline DC-3F/VCRd-5L as well as its daunorubicin-resistant subline DC-3F/DMXX were propagated in a 1:1 mixture of minimum essential medium with nonessential amino acids and of Ham's nutrient of mixture F12 supplemented with 5% fetal calf serum (Biedler, J. L. et al., Drug resistance in Chinese hamster lung and mouse tumor cells. *Cancer Treat. Rep.* 67: 859–867, 1983). All drug resistant cells were maintained in their respective drug selection media up to the day of experiment. Cell culture media and reagents were purchased from GIBCO (Grand Island, N.Y.). Adriamycin (doxorubicin) was obtained from Adria Laboratories (Columbus, Oh.). Colchicine, vincristine, and daunorubicin were purchased from Sigma Chemical Comp. (St. Louis, Mo.).

Monoclonal Antibody. Murine McAb was produced by hybridoma, the technique commonly used in our laboratory at RPMI (Goding, J. W. Antibody production by hybridomas. *J. Immunol. Methods* 39: 285–308, 1980; Papsidero, L. D. et al., Monoclonal antibodies [F36/22 and M7/105] to human breast carcinoma. *Cancer Res.* 43: 1741–1754, 1983). Briefly, BALB/c mouse (West Seneca Laboratory, Buffalo, N.Y.) were immunized, 4×, at weekly intervals by i.p. injection of a mixture of viable $2780^{AD}$ and KB-24 cells ($5\times10^6$ cells each per injection). Six months after the last i.p. injection, mouse were immunized, 2×, one week apart by i.v. injection of crude plasma membranes prepared from $2780^{AD}$, KB-24, DC-3F/VCRd-5L, and DC-3F/DMXX cells ($5\times10^6$ cells each per preparation/injection). Three days after the last i.v. injection, the fusion of splenocytes of immunized mouse with mouse myeloma cells NS1 (American Type Culture Collection, Rockville, Md.) was performed, and cultures on 96-well plates (Falcon/Becton Dickinson, Lincoln Park, N.J.). The culture supernatants were screened by ELISA on cells fixed with 2% paraformaldehyde (Sigma). Horseradish peroxidase conjugated goat anti-mouse immunoglobulin antiserum was used as the secondary antibody (Bio-Rad Laboratories, Hercules, Calif.). Antibody-secreting clones were selected which bound strongly to $2780^{AD}$, KB-24, DC-3F/VCRd-5L, and DC-3F/DMXX cells, and failed to bind to A2780, KB-3-1 and DC-3F cells. The antibody-secreting hybridoma was further cloned by the limiting dilution method. One McAb, designated F4, was purified from ascites by ammonium sulfate precipitation followed by a Protein A affinity column (Bio-Rad), according to the manufacturer's instruction. Further binding assay was performed by cell surface RIA using 2% paraformaldehyde fixed cells on Removacell strips (Dynatech Laboratories, Alexandria, Va.).

Murine McAb C219 was purchased from Centocor (Malvern, Pa.), and MRK16 was kindly provided by Dr. Takashi Tsuruo of Tokyo.

Plasma Membrane Preparation. Crude plasma membranes were prepared following a procedure as described previously by Riodan, J. R. et al., Purification of P-glycoprotein from plasma membrane fesicles of Chinese hamster ovary cell mutant with reduced colchicine permeability, *J. Biol. Chem.* 254: 12701–12705; 1979, with modification. All experiments were performed at 4° C. Adriamycin-resistant $2780^{AD}$ cells were washed with PBS (NaCl 140 mM, KCl 2.7 mM, $KH_2PO_4$ 1.5 mM, $Na_2HPO_4$ 8.1 mM, pH 7.2) and resuspended at $5 \times 10^7$ cells/ml in lysis buffer (10 mM Tris-HCl, pH 7.4, 10 mM KCl, 1.5 mM $MgCl_2$, 2 mM phenylmethylsulfonyl fluoride) for 10 min. The swollen cells were disrupted by stroking 40–50 times with Ten Broeck homogenizer (Corning 7726) until approximately 80% of cells were broken. The homogenate was centrifuged at 400 g for 10 min. to remove the cell debris. The remaining supernatant was further centrifuged at 100,000 g for 60 min. to obtain crude plasma membrane enriched fraction. Yields of >100 µg protein of plasma membrane, as determined using BSA as standard by Peterson's method (Peterson, G. L., A simplification of the protein assay method of Lowry et al. which is more generally applicable. *Anal. Biochem.* 83: 346–356, 1977), were commonly obtained from $2 \times 10^7$ cells.

Plasma membrane proteins from surgical specimens were similarly prepared. Briefly, the specimens were frozen immediately after surgery by immersion in liquid nitrogen and stored frozen at –90 C. until use. Solid tissues (40–1900 mg) were pulverized quickly to small pieces with a hammer, thawed, and homogenized in lysis buffer for the preparation of the membrane proteins as described above.

Competitive Binding-Inhibition Assay. McAb F4 and C219 were labeled individually with $^{125}I$ by the chloramine T procedure (Sonoda, S. et al., Studies of $^{125}I$ trace labeling of immunoglobulin G by chloramine T. *Immunochem.* 7: 885–898, 1970). Ten µg of McAb was iodinated by 200 µCi of $Na^{125}I$ (ICN, Irving, Calif.) in the presence of chloramine T (0.5 mg/ml). The solution was allowed to react at room temperature for 1 min. and then was stopped by the addition of sodium metabissulfite. $^{125}I$-Labeled McAb was separated from free $^{125}I$ by gel filtration on Sephadex G-50. For competitive binding-inhibition assay between $^{125}I$-labeled F4 and F4 or MRK16, Removacell plates were seeded with $2780^{AD}$ cells ($1 \times 10^5$ cells/well) for 24 hr. After washing 4× with PBS, the cells were fixed with 2% paraformaldehyde for 10 min., and washed 4× with PBS. $^{125}I$-Labeled F4 ($1 \times 10^5$ cpm/welt) and various amounts of F4 or MRK16 in 1% BSA/PBS were added to the well and incubated at room temperature for 1 hour. The plates were then washed 4× with PBS. Each individual well was cut, separated and counted in a Multi-Prias gamma counter (Packard Instruments, Downers Grove, Ill.). For competitive binding-inhibition assay between $^{125}I$-labeled C219 and C219 or F4, crude plasma membrane preparation was used to coat each well (5 µg protein/well) by drying at 37 C. overnight on Millititer HA plates (Millipore Corp., Bedford, Mass.). After blocking the unsaturated sites with 1% BSA/PBS for 1 hr, $^{125}I$-labeled C219 ($1 \times 10^5$ cpm/well) and various amounts of C219 or F4 in 1% BSA/PBS were added to the well and incubated at room temperature for 1 hour. The plates were washed, and each individual well was cut and the radioactivity of each well was counted. Binding inhibition in % was calculated according to the following formula (Gerhard, W. et al., Application of monoclonal antibodies in virology. In: Weir, D. M. (ed.), *Handbook of Experimental Immunology*, Vol. 4, pp 115.1–115.13. London: Blackwell Sci. Publ, 1986; Chu, T. M. et al., Prostate-specific antigen domain of human prostate specific antigen identified with monoclonal antibodies. *J. Urol* 141: 152–156, 1989):

$$\left(1 - \frac{\text{cpm bound by labeled antibody in the presence of unlabeled antibody}}{\text{cpm bound by labeled antibody in the absence of unlabeled antibody}}\right) \times 100$$

The maximal binding was obtained by using 1% BSA/PBS in the absence of unlabeled antibody.

Chemical and Enzymatic Treatment: Crude plasma membrane prepared from $2780^{AD}$ cells was coated on Millititer HA plates (2.5 µg protein/well), and subjected to various treatments of chemical modification and enzymatic hydrolysis (Meyers, M. B. et al.; Papsidero, L. D. et al., Immunoaffinity isolation of ductal carcinoma antigen using monoclonal antibody F36/22. *Mol. Immunol.* 21: 955–960, 1984). Plasma membrane preparation was subjected to heat treatment (45 C. for 3 hr.) in the presence of 8M urea, and 6M guanidine-HCl with or without 10 mM dithiothreitol and 20 mM iodoacetic acid. The effects of proteolytic enzymes were assessed by incubating plasma membrane preparation with enzyme in a final volume of 100 µl of appropriate buffer system at room temperature for 1 hr. The following enzymes (final concentration) were tested: pronase (100 U/ml, Boehringer Mannheim, Indianapolis, Ind.), and trypsin (2.5 µg/ml, GIBCO). The treatment with neuraminidase (Type V 20 µU/ml, Sigma) was allowed to proceed for 1 hr. at 37 C. Additionally, plasma membrane preparation was treated with methanol at room temperature for 1 hr, and with 1 mM sodium periodate followed with 10 mM sodium borohydride at 25 C. for 30 min. each. Appropriate control was performed simultaneously for each experiment. After each treatment, the well was washed 4× with PBS, and incubated with $^{125}I$-labeled McAb F4 ($1 \times 10^5$ cpm/well) at room temperature for 1 hr. Effects of the treatment in % inhibition were then calculated from the untreated control.

Indirect Immunofluorescence Staining. Cells ($4 \times 10^7$) were washed 4× with PBS, and fixed with 2% paraformaldehyde in a microtube (1.5 ml, Sarstedt, Princeton, N.J.) for 10 min. After washing 4× with PBS, cell suspension was incubated with 200 µl of McAb (20 µg/ml) for 45 min. on ice, washed 4× with cold PBS, and then stained for 45 min. on ice with 200 µl of 1:40 fluorescein isothiocyanate-conjugated goat anti-mouse immunoglobulin antiserum (Becton Dickinson, San Jose, Calif.). After washing, cells were mounted in permafluor mounting medium (Lipshaw Immunon, Detroit, Mich.). The slides were examined by a Bio-Rad MRC 600 Laser Scanning Confocal Imaging System (Bio-Rad, Cambridge, Mass.). Ten or more fields were examined in each specimen. Cells were scanned in 1-µm-thick optical sections to determine the distribution of McAb stained components. Images of 1-µm sections were collected in digitized form from regions of interest, and stored in computer. For photography, 2–3 images of consecutive 1-µm sections were integrated and projected as a single fixed image (Weiss, L. et al., Effects of cytosketal perturbation on the sensitivity of Ehrlich ascites tumor cell surface membranes to mechanical trauma. *Invasion Metas.* 11: 93101, 1991).

Immunoblot Analysis. Crude plasma membrane proteins were separated by electrophoresis in a 7.5% SDS polyacrylamide gel (Laemmli, U.K., Cleavage of structural proteins during the assembly of the head of bacteriophage T4. *Nature* (Lond.) 227: 680–685, 1970). Proteins in gels were electroblotted in nitrocellulose membranes (Towbin, H. et al., Electrophoretic transfer of proteins from polyacrylamide gels to nitrocellulose sheets: procedure and some applications. Proc. Natl. Acad. Sci. USA 76: 4350–4354, 1979). The blots were blocked with 5% nonfat milk in PBS, and the nitrocellulose was incubated at room temperature for 1 hr with antibody (5 µg/ml) in PBS containing 5% BSA. After a brief wash, the nitrocellulose was incubated with 1:3000 dilution of peroxidase conjugated sheep anti-mouse immunoglobulin (Amersham, Arlington Heights, Ill.) in blocking buffer containing 0.1% Tween-20 at room temperature for 1 hr. Following an extensive wash, the immobilized antigen was detected by an enhanced chemiluminescence kit (Amersham) according to the manufacturer's instruction. The molecular weight references used were myosin (Mr 200,000), phosphorylase b (Mr 97,000), BSA (Mr 68,000), and ovalbumin (Mr 43,000).

Immunoprecipitation. Crude plasma membrane proteins from $2780^{AD}$ or A2780 cells (800 µg each) were mixed with McAb F4 or normal mouse immunoglobin (80 µg each) in a final volume of 0.6 ml PBS containing 0.1% Triton X-100, and gently shaken by inversion at 4 C. for 3 hr. Then, 0.5 ml of immunobeads coated with rabbit anti-mouse immunoglobulin (Bio-Rad) were added to each mixture and gently shaken at 4 C for 3 hr. The precipitates were washed extensively with PBS containing 0.1% Triton X-100. The precipitated proteins were dissociated by incubating with 200 µl of sample treatment buffer (125 mM Tris, pH 6.8, 20% glycerol, 2% SDS, 2% 2-mercaptoethanol and 0.01 mg/ml Bromphenol blue) at 100 C for 5 min. Subsequently, the samples containing dissociated proteins were analyzed by gel electrophoresis in reducing condition and immunobloted with McAb C219 as described above.

Flow Cytometry. Staining of the cells was performed as follows: 1×10⁸ cells were fixed in 1% paraformaldehyde in PBS for 30 min. on ice or without fixation. Cells were washed with PBS, and incubated with 100 µl of normal goat serum for 30 min. on ice in order to reduce the nonspecific binding. Then cells were washed and incubated with McAb (10 µg/ml) on ice for 30 min. Background fluoroescence was determined by incubating the cells with normal mouse immunoglobulin. After washing with PBS, cells were stained on ice for 30 min. in 200 µl of 1:40 fluorescein isothiocyanate-conjugated goat anti-mouse immunoglobulin antiserum. Fluorescence analysis of stained cells were performed with a FACSTAR PLUS flow cytometer (Becton Dickinson).

Other Techniques. Isotype of McAb was determined by ELISA using a commercial kit (Zymed Laboratories, San Francisco, Calif.). Indirect immunoperoxidase staining was performed by a procedure described previously (Croghan, G. A. et al., Tissue distribution of an epithelial and tumor-associated antigen recognized by monoclonal antibody F36/22. *Cancer Res.* 43: 4980–4988, 1993).

RESULTS *Binding of Monoclonal Antibody F4 to Cultured Cells.* Hybridoma culture of F4, derived from immunization of mouse with adriamycin and colchicine resistant human tumor cells, and vincristine and daunorubicin resistant hamster lung cells, was screened by ELISA and subcloned by limiting dilution method. A clone of IgGl isotype was eventually generated. Specific binding activity of McAb F4 was further assessed against a panel of drug resistant and drug-sensitive cell lines. Using cell surface RIA and as shown in Table 1, McAb F4 produced a strong reaction (20,000 cpm, 100%) with human ovarian carcinoma cell line resistant in vitro to adriamycin, $2780^{AD}$, and a negligible reaction with its drug sensitive parental line A2780 (600 cpm, 3%).

TABLE 1

Cell surface binding of monoclonal antibody F4[a]

| Target cell | | maximum binding activity (in %)[b] |
|---|---|---|
| $2780^{AD}$ | (adriamycin resistant) | 100 |
| A2780 | (adriamycin sensitive) | 3 |
| KB-24[c] | (colchicine resistant) | 78 |
| KB-100 | (colchicine resistant) | 58 |
| KB-10 | (colchicine resistant) | 39 |
| KB-5 | (colchicine resistant) | 39 |
| KB-3-1 | (colchicine sensitive) | 11 |
| MCF-7$^{AD}$ | (adriamycin resistant) | 48 |
| MCF-7 | (adriamycin sensitive) | 14 |
| DC-3F/VCRd-5L | (vincristine resistant) | 73 |
| DC-3F/DMXX | (daunorubicin resistant) | 43 |
| DC-3F | (drug sensitive) | 6 |

[a]Cells were plated (1 × 10⁵ cells/well) in 96 well Removacell strip and allowed to grow for 24 hours to form an attached cell monolayer. Cells were washed with PBS and fixed with 2% paraformaldehyde at room temperature for 10 minutes. Plates were washed again with PBS and blocked with 1% BSA in PBS. Fifty µl of $^{125}$I-labeled F4 (1 × 10⁵ cpm/well) was added and incubated for 3 hours.
[b]Maximum binding (100%) represented the target cell line binding the most $^{125}$I-labeled McAb F4, and binding to other target cells was expressed relative to that level. The maximum binding in cpm (mean of three experiments) was to $2780^{AD}$ at 2 × 10⁴.
[c]Colchicine concentration in culture medium: KB-24 1 µg/ml, KB-100 100 ng/ml, KB-10 10 ng/ml, KB-5 5 ng/ml, and KB-3-1 none.

McAb F4 also bound significantly with colchicine resistant cell line KB-24 (cultured in the presence of colchicine 1 µg/ml), KB100 (100 ng/ml), KB-10 (10 ng/ml), and KB-5 (5 ng/ml), but weakly with colchicine sensitive parental cell line KB-3-1. Similar strong vs weak results were detected when tested against adriamycin resistant human breast carcinoma cell line MCF-7$^{AD}$ vs adriamycin sensitive MCF-7, and against vincristine resistant hamster lung cell line DC-3F/VCRd-5 and daunorubicin resistant cell line DC-3F/DMXX vs drug sensitive parental cell line DC-3F. It is clear from these results that McAb F4 reacted significantly with drug resistant cell lines, whether it was derived from the resistance to adriamycin, colchicine, vincristine, or daunorubicin, and reacted insignificantly, if any at all, with drug sensitive parental cell lines.

Table 1 also shows that, at least from its quantitative binding activity to KB carcinoma cell line series, the degree of antibody F4 finding activity appeared to be inversely proportional to the degree of drug sensitivity of the target cells; i.e. the greater the drug resistance, the stronger was the binding activity.

In addition to cell surface RIA, the binding activity of F4 was examined by immunoperoxidase staining (Croghan, G. A. et al). McAb F4 at 4 µg/ml was shown to stain very intensively (+++), mostly along the area of cell surface, of a significant number of $2780^{AD}$ cells and of KB-24, whereas no stain (−) was detected with A2780 cells or KB-3-1 cells.

Figure 1A:
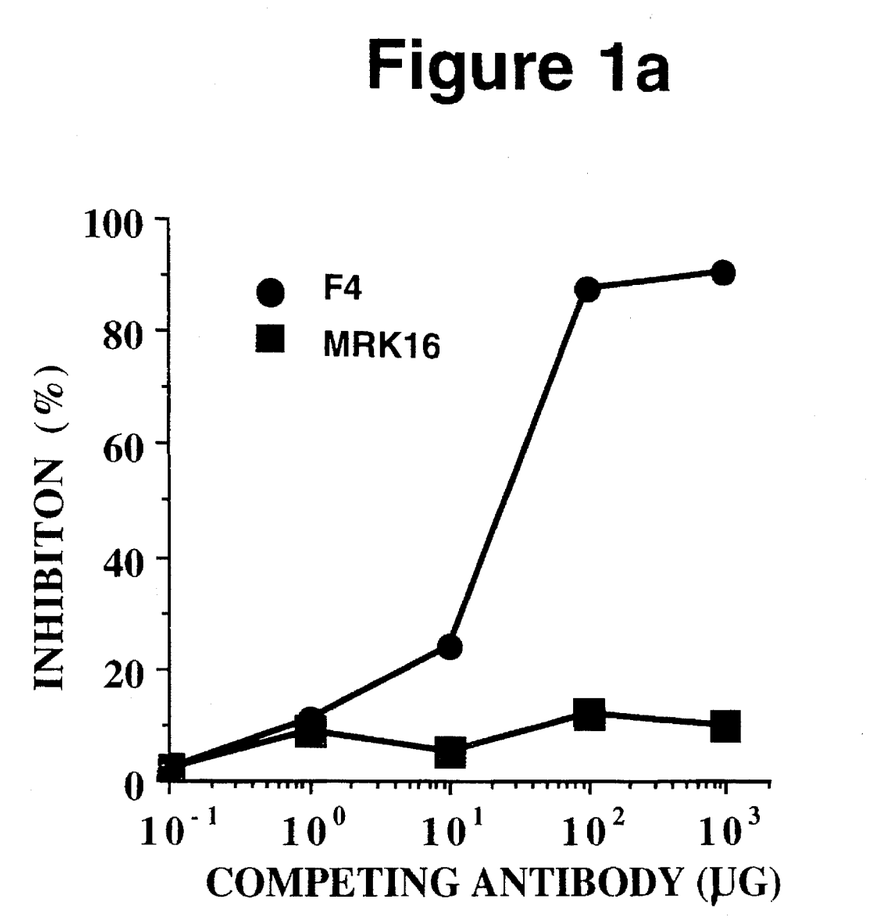
FIG. 1a is a graph of compention of McAb F4 with MRK16 for $2780^{AD}$ cancer cells.
Figure 1B:
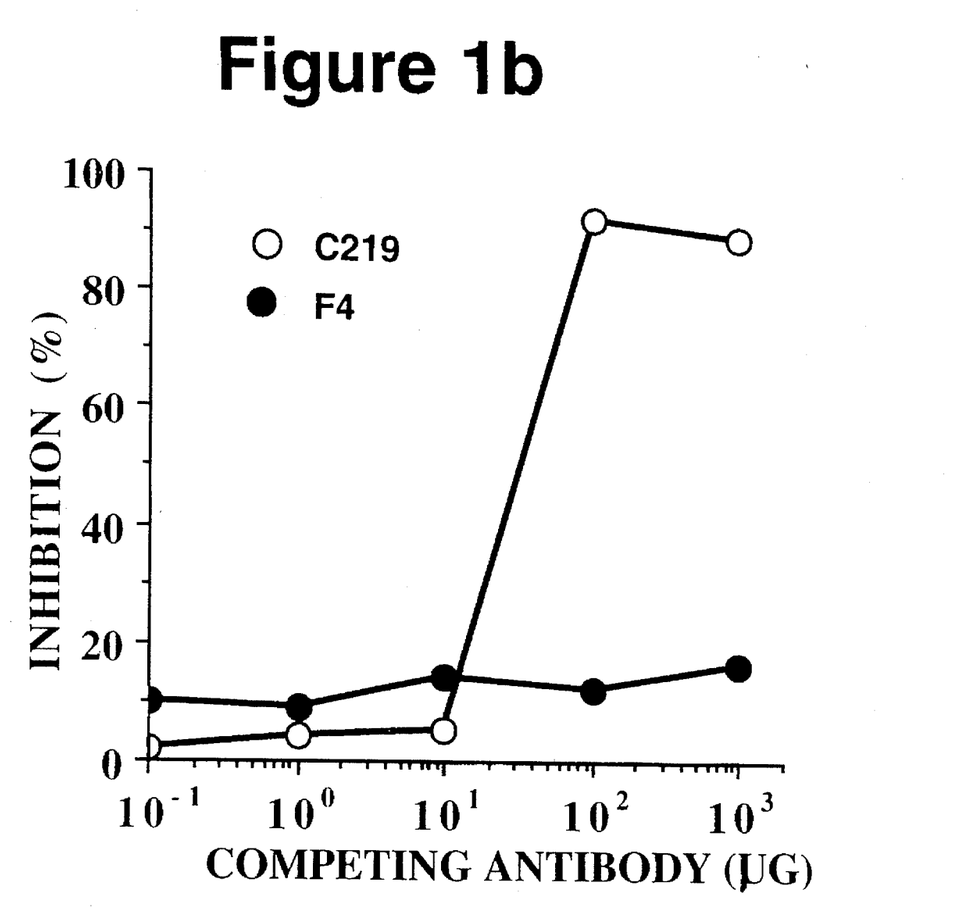
FIG. 1b is a graph of competition of McAB F4 with C219 for $2780^{AD}$ cancer cells.

Competitive Binding-Inhibition Experiments. Next studied, was whether McAb F4 recognized the same or a different antigenic determinant from those recognized by two commonly known McAb associated with multidrug resistance, C219 and MRK16 (5,7). For this purpose, McAb F4 and C219 were individually radio-iodinated with $^{125}$I, and competitive binding-inhibition experiments were performed using $2780^{AD}$ cells as the target antigen source and unlabeled McAb F4, MRK16, and C219 as the competing antibodies. In particular, the tests shown in FIGS. 1a and 1b were prepared as follows:

FIG. 1a: Removacell plates were seeded with $2780^{AD}$ cells ($1\times10^5$ cells/well) for 24 hours. After washing with PBS, the cells were fixed with 2% paraformaldehyde. $^{125}$I-Labeled McAb F4 ($1\times10^5$ cpm/well) and various amounts of unlabeled MRK16 (■), or F4 (●), as indicated in 1% BSA/PBS were added to the well and incubated at room temperature for 1 hour. The plates were washed with PBS, and each individual well was cut and radioactivity in each well was counted in a gamma counter. Binding-inhibition in was calculated according to the formula: (1-(cpm bound by labeled antibody in the presence of unlabeled antibody/cpm bound by labeled antibody in the absence of unlabeled antibody)) x 100. FIG. 1b: Crude plasma membrane prepared with $2780^{AD}$ cells was used to coat each well (5 μg protein/well) of Millititer HA plates by drying at 37 C overnight. After blocking the unsaturated sites with 1% BSA in PBS, $^{125}$I-labeled C219 ($1\times10^5$ cpm/well) and various amounts of C219 (o), or F4 (●), as indicated in 1% BSA/PBS were added to the well and incubated at room temperature for 1 hour. The plates were washed and each individual well was cut and radioactivity in each well was counted. Binding-inhibition in % was calculated as described.

FIG. 1a reveals that, using the technique of cell surface RIA, McAb MRK16 at a large range of quantity failed to inhibit the binding activity of $^{125}$I-labeled McAb F4 to $2780^{AD}$ cells, whereas unlabeled F4 completely inhibited the binding of $^{125}$I-labeled F4 to $2780^{AD}$ cells. This result indicated that the antigenic determinant recognized by McAb F4, or F4 epitope, is different from that of McAb MRK16.

In initial experiment, McAb C219 was shown to react negatively with intact $2780^{AD}$ cells, but positively with plasma membrane prepared from $2780^{AD}$ cells. Using crude plasma membrane preparation of $2780^{AD}$ cells as the target antigen source in binding-inhibition experiments of $^{125}$I-labeled McAb C219 to $2780^{AD}$ cells by McAb C219 or F4, the results, as shown in Figure 1b, indicated that McAb F4 at a large range of quantity failed to inhibit the binding activity between $^{125}$I-labeled McAb C219 and $2780^{AD}$ where unlabeled C219 completely inhibited the binding of $^{125}$I-labeled C219 to $2780^{AD}$ cells. The results from these competitive binding-inhibition experiments therefore demonstrate that the antigenic determinant recognized by McAb F4 is distinct from those of McAb C219 and MRK16, which recognize an intracellular and an extracellular epitope of P-glycoprotein in multidrug-resistant human tumor cells, respectively (Kartner, N. et al.; Hamada, H. et al.).

Chemical Modification and Enzymatic Digestion. The antigenic determinant of McAb F4 was partially characterized as follows. Plasma membrane preparation of $2780^{AD}$ cells was subjected to chemical and enzymatic treatments as summarized in Table 2.

TABLE 2

Effects of chemical modification and enzymatic hydrolysis on binding activity of McAb F4[a]

| Treatment | Binding Activity (%) |
| --- | --- |
| 1. Untreated control | 100 |
| 2. 6 M guanidine-HCl, 45 C., 3 hr | 0 |
| 3. 6 M guanidine-HCl, 10 mM dithiothreitol, 45° C., 3 hr; 20 mM iodoacetic acid, 25° C., 30 min. | 0 |
| 4. Methanol, 25° C., 1 hr. | 0 |
| 5. Pronase 100 U/ml, 25° C., 1 hr. | 0 |
| 6. 8 M urea, 45° C., 3 hr. | 10 |
| 7. Trypsin 2.5 μg/ml, 25° C., 1 hr. | 100 |
| 8. Neuraminidase 20 μU/ml, 25° C., 1 hr. | 100 |
| 9. 1 mM sodium periodate, 25° C., 30 min.; 10 mM sodium borohydride, 25° C., 30 min. | 10 100 |

[a]Crude plasma membrane prepared from $2780^{AD}$ cells was coated on Millititer HA plates (25 μg protein/well), and subjected to various treatments as indicated, then binding activity of $^{125}$I-labeled McAb F4 to treated plasma membrane was measured. Untreated control for each treatment was performed simultaneously and used to calculate the binding activity in %.

$^{125}$I-Labeled McAb F4 was then allowed to react with the chemically modified or enzymatically hydrolyzed plasma membrane preparation. The results revealed that the antigenic determinant of McAb F4 was sensitive to the treatment of 6M guanidine—HCl, 8 M urea, methanol, and pronase, and was resistant to the modification of sodium periodate oxidation followed by sodium borohydride reduction, and digestion of neuraminidase, and of trypsin. These results thus suggest that F4 epitope is potentially located at or involved in the conformational structure of the antigen molecule.

Cell Surface Localization of F4 Epitope. The original goal was to generate McAb(s) which recognize cell surface epitope(s) of drug resistant cell lines, as it can be noted from the selection of procedures used in the handling of immunogen preparation and hybridoma screening. Subcellular localization of the epitope recognized by McAb F4 was performed by indirect immunofluorescence. As examined initially by conventional fluorescence microscope, McAb F4 labeled viable $2780^{AD}$ cells were observed to produce a highly intensive fluorescence, suggesting that F4 detected a nonpermeable and probably cell surface epitope.

Figure 2:
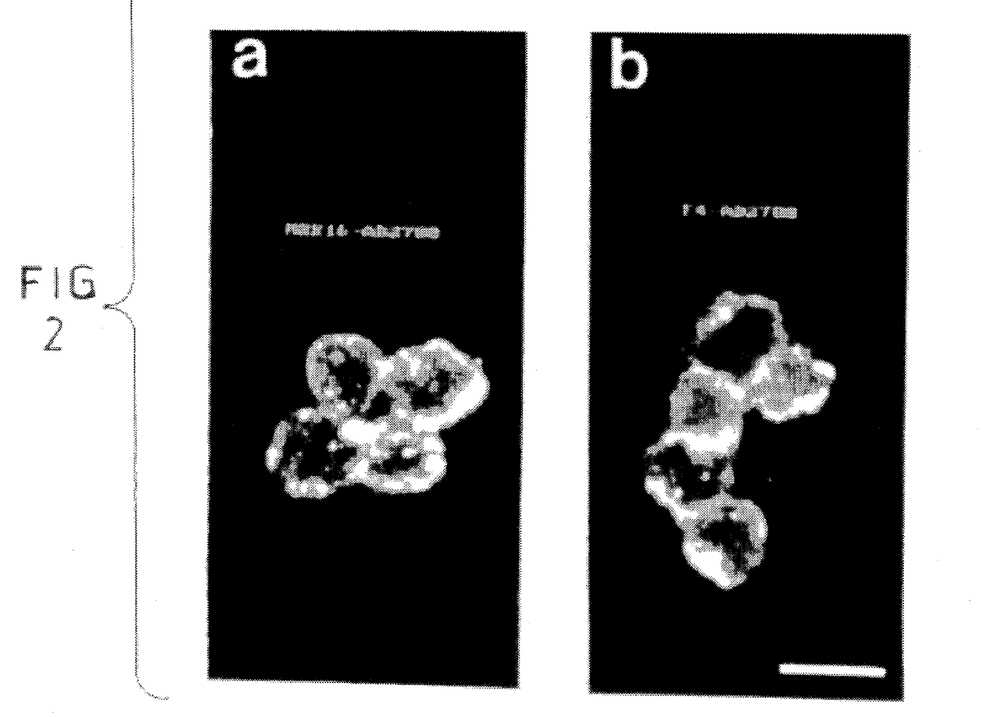
FIG. 2 is two plates showing the results of laser scanning confocal imaging to show localization of the F4 epitope.

To confirm the extracellular localization of the F4 reactive epitope, a more powerful laser scanning confocal imaging system than a conventional microscope was employed to examine the F4 stained fluorescence of $2870^{AD}$ cells, and also of KB-24 cells. Adriamycin-resistant human ovarian carcinoma cells $2780^{AD}$ grown for 24 hours on chamber slides were fixed with 2% paraformaldehyde, washed with PBS, and then incubated with McAb for 45 minutes, washed with PBS, and overlaid with fluorescein isothiocyanate-conjugated goat anti-mouse immunoglobulin antiserum for 45 minutes. After washing, cells were mounted in permafluor mounting medium. The slides were examined by a Bio-Rad MRC 600 Laser Scanning Confocal Imaging System, which revealed the staining of $2780^{AD}$ cells by McAb MRK16 (panel a), and by McAb F4 (panel b). Bar=10 μm for both a and b. The results obtained from McAb F4, as compared with those from McAb MRK16, revealed that both McAb F4 and MRK16 reacted with both $2780^{AD}$ cells and KB-24 cells, and did not react with A2780 cells or KB-3-1 cells. As shown in FIG. 2, the reactivity pattern and cell surface fluorescence of $2780^{AD}$ cells with F4 is very similar to that of MRK16, although the cell surface labeling with MRK16 is more uniform that that with F4. No stain in the cytoplasm or nucleus was noted with F4 or MRK16. The cell surface nonreactive antibody C219 was used as control and revealed no cell surface labeling with either $2780^{AD}$ or KB-24 cells (data not shown). These observations indicate that McAb F4, just like MRK16 (Willingham, M. C. et al., Immunocytochemical localization of P170 at the plasma membrane of multidrug-resistant human cells. *J. Histochem. Cytochem.* 35: 1451–1456, 1987), detects a determinant exposed on the external surface of plasma membranes.

Additional evidence obtained from flow cytometry was provided to further ascertain the extracellular nature of F4 epitope localization. Again, using McAb MRK16 and C219 as positive and negative control, respectively, results indicated that McAb F4 was reactive with a cell surface antigenic determinant, different from that of MRK16, of $2780^{AD}$ and KB-24 cells, and that neither F4 nor MRK16 reacted with drug-sensitive A2780 or KB-3-1 cells (data not shown). Moreover, flow cytometry also revealed that McAb C219 showed no cell surface binding on either $2780^{AD}$ A2780 or KB-24, KB-3-1 cells.

Figure 3:
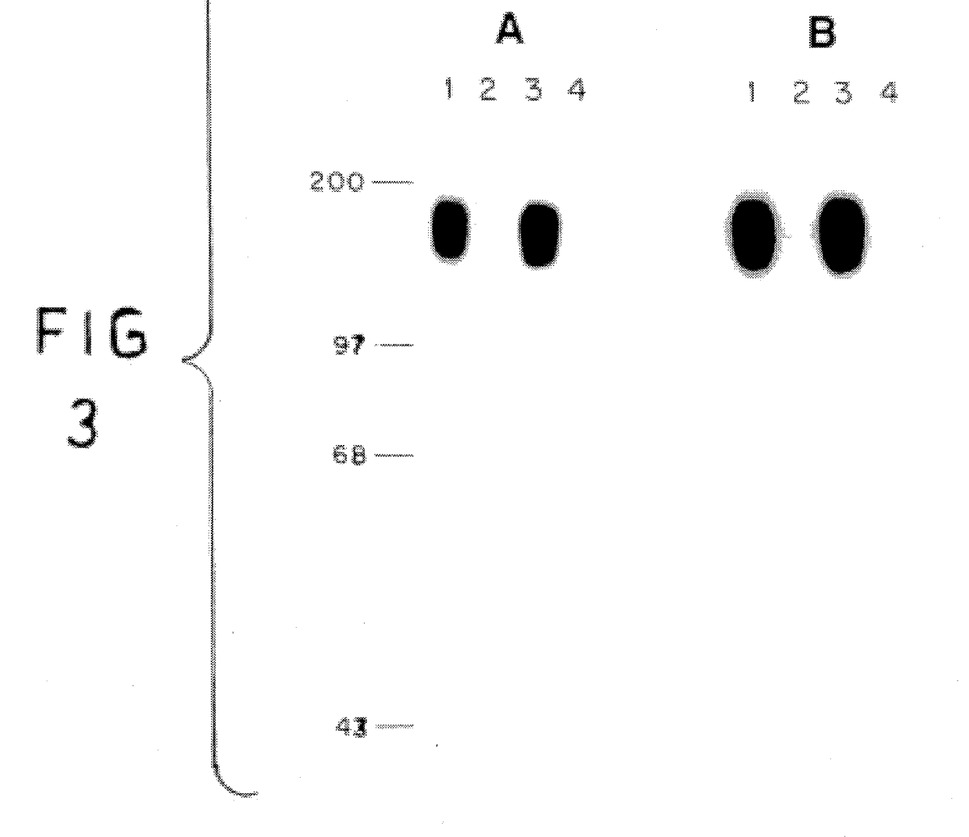
FIG. 3 shows comparative immunoblots for McAB F4 and C219 against drug resistant P-glycoprotein producing cell lines with nonresistant drug lines which do not produce P-glycoprotein.

Immunoreactivity of McAb F4 with P-glycoprotein. Crude plasma membrane proteins prepared from $2780^{AD}$ A2780, KB-24, and KB-3-1, were subjected to SDS-PAGE, transferred to nitrocellulose, and then immunoblotted by McAb F4 or control antibody C219. In particular, as to obtain the results shown in FIG. 3, crude plasma membrane proteins (30 µg/lane) from $2780^{AD}$(lane 1), 2780 (lane 2), KB-24 (lane 3), and KB-3-1 cells (lane 4), were subjected to 7.5% SDS-PAGE, transferred to nitrocellulose, and immunoblotted with McAb F4 (A) or C219 (B). Blots were incubated with peroxidase conjugated sheep anti-mouse immunoglobulin. After washed extensively, the blots were detected by an enhanced chemiluminescence procedure. Molecular weight references are shown at the left. The experiments were repeated three times with the same results as shown. FIG. 3 (panel A) indicates that an immunoreactive band, approximately with a Mr 170,000–180,000, was detected by F4 in the plasma membrane preparations of $2780^{AD}$ (lane 1) and of KB-24 (lane 3) cells, but was absent in that of A2780 (lane 2) and of KB-3-1 (lane 4) cells. Similar results were obtained from C219 (FIG. 3, panel B). Since McAb C219 is a McAb specific or P-glycoprotein (Juranka, P. F. et al.; Kartner, N. et al.), these results suggested that McAb F4 also reacts with P-glycoprotein.

Figure 4:
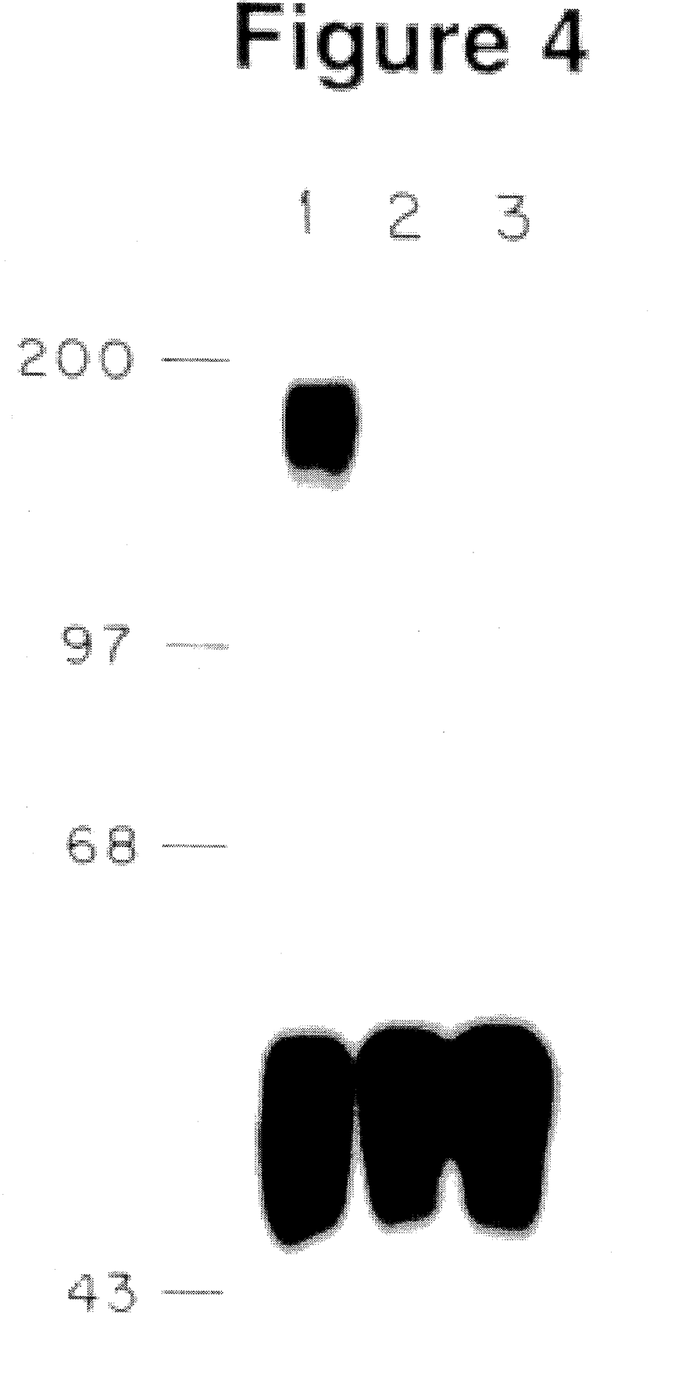
FIG. 4 shows immunoblots of McAB F4 and C219 precipitated plasma membrane proteins.

To confirm the immunoreactivity of McAb F4 with P-glycoprotein, crude plasma membrane proteins prepared from $2780^{AD}$cells were allowed to react with F4 and then precipitated by rabbit anti-mouse immunoglobulin in solid-phase. The antigen- antibody complexes were further subjected to SDS-PAGE and finally immunoblotted with C219.

In particular, to obtain the results shown in FIG. 4, crude membrane proteins (800 µ g) from $2780^{AD}$ cells (lane 1) and A2780 (lane 3) were incubated with McAb F4 (80µg) at 4 C for 3 hours. Control precipitation was performed with the mixture of crude plasma membrane proteins from $2780^{AD}$ cells and normal mouse immunoglobulin (lane 2). Immunobeads coated with rabbit anti-mouse immunoglobulin were added to the mixture and incubated at 4 C for an additional 3 hours. The precipitates were washed extensively and the precipitated proteins were dissociated in 200 µl of SDS-PAGE sample treatment buffer. Forty µl of samples containing the dissociated proteins were subjected to 7.5% SDS-PAGE in reducing condition, transferred to nitrocellulose, and immunoblotted with McAb C219. Blots were incubated with peroxidase conjugated sheep anti-mouse immunoglobulin. After washed extensively, the blots were detected by an enhanced chemiluminescence procedure. Molecular weight references are shown at the left. The experiments were repeated three times with the same results as shown. FIG. 4 reveals that the antigenic molecule which was precipitated by F4 was reactive with McAb C219 (lane 1). Control samples, e.g. $2780^{AD}$ reacted with control mouse IgG (lane 2) and control cells A2780 reacted with F4 (lane 3) were negative in immunoblotting with C219. The broad apparently overloaded band detected at Mr 45–55,000 in all three lanes represent that of dissociated heavy chain of murine IgG; and the light chain (Mr 25,000) was not detectable under the present experimental condition. Overall, these results (FIG. 3 and FIG. 4) indicated that McAb F4 is reactive with P-glycoprotein, and that F4 epitope is distinct from C219 epitope.

Figure 5:
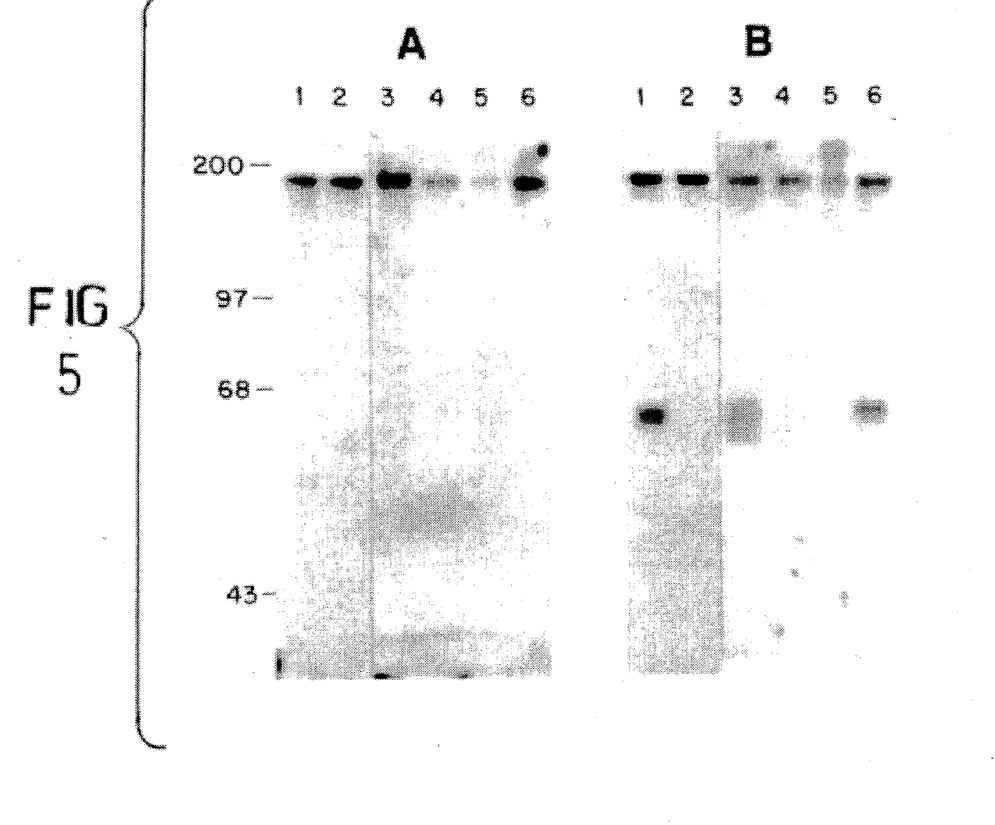
FIG. 5 shows immunoblots of crude plasma membrane proteins from individual cancer patients with F4 (panel A) and C219 (panel B).

To investigate the possible clinical application of F4, crude plasma membrane proteins prepared from 6 individual cancer patients' surgical specimens were immunoblotted with F4 after being subjected to SDS-PAGE and transferred to nitrocellulose. The results were compared with those obtained with C219. In particular, individual specimens of plasma membrane proteins (50 µg/lane) from 6 patients were subjected to 7.5% SDS-PAGE, transferred to nitrocellulose, and immunoblotted with McAb F4 (A) and C219 (B). Blots were incubated with peroxidase conjugated sheep anti-mouse immunoglobulin. The immobilized antigens were detected by an enhanced chemiluminescence procedure. Molecular weight references are shown at the left. The experiments were repeated twice with the same results as shown. Primary diagnosis was: sarcoma (lane 1), malignant lymphoma (lane 2), adenocarcinoma of the lung (lanes 3 and 6), anaplastic small cell carcinoma of the lung (lane 4), and undifferentiated carcinoma of the jugular nodes (lane 5). All 6 specimens were shown to exhibit varying degrees of reactivity with F4 (FIG. 5, panel FIG. 5 (panel B) also shows that an additional band located approximately at Mr 63,000 was reactive with C219 (lines 1, 3, and 6), but nonreactive with F4. F4 also was shown to stain, by immunoperoxidase technique, the conventionally prepared formalin-fixed and paraffin-embedded tissue sections (data not shown), thus enhancing its potential clinical use.

Figure 6:
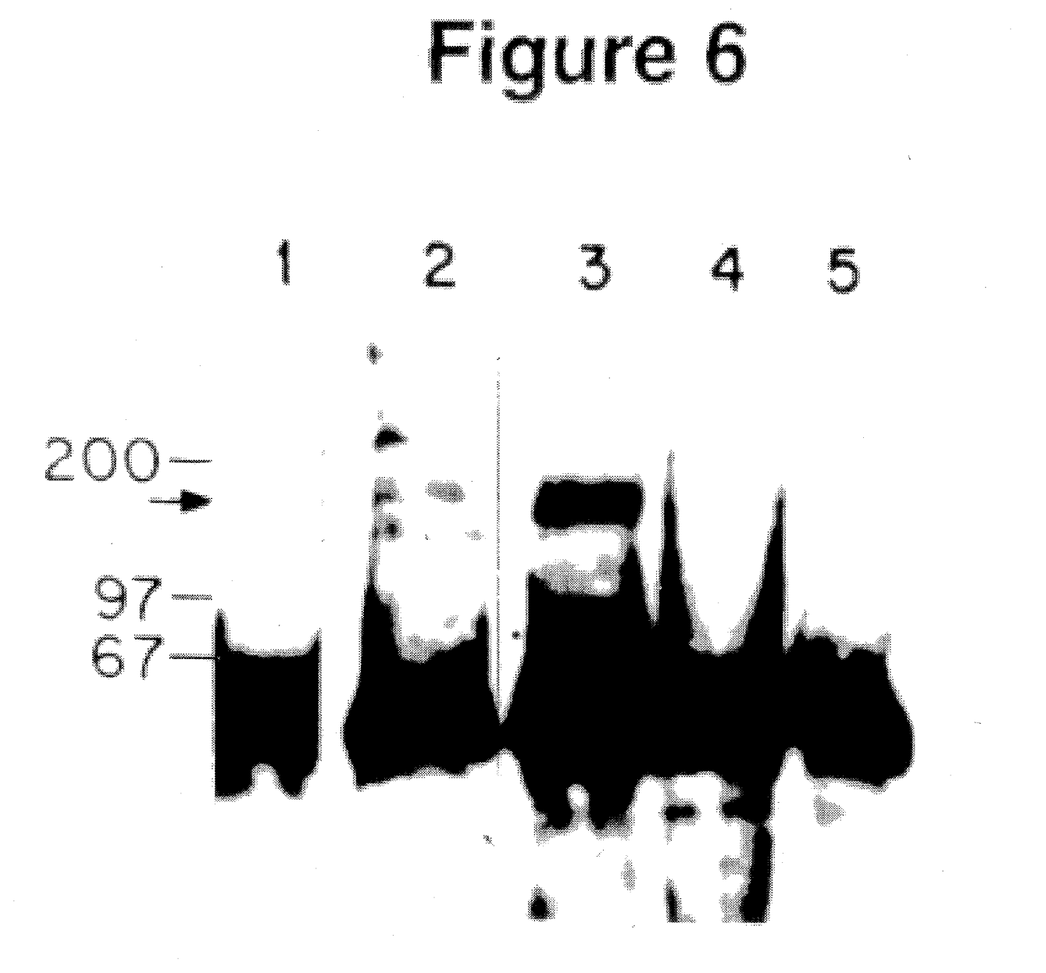
FIG. 6 shows immunoblots of human breast cancer ascites with F4 and various other antibodies.

Reactivity with soluble P-glycoprotein in ascites of McAb F4. Human breast cancer ascites 1 ml was centrifuged at 10,000 × g at 4 C for 5 minutes. Supernatant was collected and added with 50 µg of McAb each F4, MRK16, C219, JSB-1, and control normal mouse IgG, and incubated at 4 C for 3 hours (top bottom mixer). Thereafter, 4 mg (in 400 µl) of rabbit anti-mouse immunoglobulin (Immunobead, Bio-Rad) were added to each specimen and incubated at 4 C for 1 hour. After centrifugation at 5,000× g at 4 C. for 3 minutes, the precipitated pellet was collected and washed/centrifuged 4× with PBS. The pellet was resuspended in 50 µl of sample buffer containing mercaptoethanol and boiled for 5 minutes, and the supernatant containing the dissociated proteins was subjected to 7.5% SDS-PAGE according to Laemli. Proteins were transferred to a nitrocellulose membrane for 1 hour at 100 V and immunoblotted with McAb F4 (4 µg/ml), C219 (1 µg/ml), and JSB-1 (5 µg/ml), respectively, for 45 minutes. Blots were incubated for 45 minutes with peroxidase conjugated goat anti-mouse IgG diluted 1:3000 and detected by an enhanced chemiluminescence procedure (Amersham). Lanes #1, 2, 3, 4 and 5, as shown in FIG. 6, were precipitated by normal mouse IgG, MRK16, F4, C219, and JSB-1 and then blotted by F4, F4, F4, C219, and JSB-1, respectively (i.e. lane #1 normal mouse IgG-F4, #2 MRK16-F4, #3 F4-F4, #4 C219-C219, #5 JSB-1-JSB-1).

As noted, the only positive result was obtained from lane #3, i.e. only McAb F4, not MRK16, C219, or JSB-1, is able to bind and precipitate and thus detect soluble P-glycoprotein from an ascite specimen. Normal mouse IgG served as a negative control.

While searching for cell surface antigenic determinants associated with multidrug resistance by means of McAb, we have derived a new murine McAb, designated F4. F4 has been found to react preferentially and significantly with a cell surface epitope in several series of multidrug resistant cells, while an insignificant reactivity is detected in their drug sensitive counterparts. It is serendipitous that McAb F4 turns out to react with P-glycoprotein, a key biochemical molecule responsible for multidrug resistance and surprising that F4 reacts with a soluble form of P-glycoprotein. Our observations would indicate that P-glycoprotein in fact is a strongly immunogenic molecule, or that the portion of P-glycoprotein exposed externally on plasma membranes is strongly immunogenic. The immunization procedure (Goding, J. W.; Papsidero, L. D. et al.), which we have used in this study, involves one primary and three i.p. immunizations of viable drug resistant cells, followed by a "rest" of six months for the mouse, then two i.v. boostings of crude plasma membranes prepared from drug resistant cells three days prior to fusion when antigen-induced proliferation of B cells is strongest. Combining with proper screening technique, this procedure proves effective in generating McAb directed against P-glycoprotein.

Several McAb to P-glycoprotein have been reported, such as C219 (5), 265/F4 (6), MRK16 (7), JSB-1 (8), HYB-241 (9), C494 and C32 (Georges, E. et al., Detection of P-glycoprotein insoforms by gene-specific monoclonal antibody. *Proc. Natl. Acad. Sci. USA* 87: 152–156, 1990). Among these well characterized McAb, MRK16 is best known for its reactivity with an extracellular epitope of P-glycoprotein. In comparison, McAb F4 is shown also to detect an extracellular epitope but different from that of MRK16. This conclusion is based upon the results obtained from competitive binding-inhibition assay, flow cytometry, and laser scanning confocal imaging analysis. Additionally, data is presented to reveal the difference between F4 and C219, although C219 is well known for its reactivity with an intracellular epitope, and so is JSB-1, C494 and C32. The 265/F4 epitope appears to be of extracellular nature, but it is sensitive to formalin fixing and paraffin embedding, whereas F4 epitope is resistant to such a treatment. Our data and that available in literature also indicate the difference between F4 and HYB-241, which is sensitive to periodate oxidation and borohydride reduction. Further, F4 is distinct from a less known cell surface McAb 32G7, based upon their different immunoprecipitation patterns (Danks, M. K. et al., Monoclonal antibodies to glycoproteins of Vinca alkaloid-resistant human leukemic cells. *Cancer Res.* 45: 3220–3224, 1985). Therefore, F4 represents a new McAb against P-glycoprotein.

Further, as shown herein, McAb F4 reacts with a soluble P-glycoprotein, while others, e.g. MRK16, C219 and JCB-1 do not. No other McAb has been reported to react with a soluble form of P-glycoprotein.

From the putative structure of the mdrl protein and its orientation in the cell membrane, extracellular component of the cell membrane occupied by P-glycoprotein is proposed to comprise two groups of three transmembrane loops each crossing the membrane six times, i.e. a total of six transmembrane loops (Chen, C. J. et al., Internal duplication and homology with bacterial transport proteins in the mdrl (P-glycoprotein) gene from multi-drug resistant human cells. *Cell* 47: 381–389, 1986). From nucleotide sequence and deduced amino acid sequence, the peptides of the six loops exposed extracellularly are identified as follows: the first loop between transmembrane segments 1 and 2 is consisted of amino acids #73-#199; second loop between transmembrane segments 3 and 4 #210-#215; 3rd loop between transmembrane segments 5 and 6 #318-#325; 4th loop between transmembrane segments 1a and 2a #732-#756; 5th loop between transmembrane segments 3a and 4a #852-#855 IYGW; and the 6th loop between transmembrane segments 5a and 6a is consisted of amino acids #958-#973.

The first loop, which is closest to the amino terminal, contains a cluster of putative N-linked glycosylation sites. Since neuraminidase treatment and periodate oxidation and borohydride reduction do not alter the binding activity of F4, F4 epitope is more likely located in the other loops. The 2nd and 5th loop each is consisted of only six and four amino acids, respectively, they are unlikely the candidates of antigenic determinant. Additionally, our data on chemical modifications and enzymatic hydrolyses indicate that the antigenic site is associated with conformational structure of P-glycoprotein molecule. Therefore, the most likely peptide where F4 epitope is localized would be in or near the 3rd, or 6th loop. It is entirely feasible to map the exact location of F4 epitope by genetic or synthetic peptide approach (Juranka, P. F. et al.; Georges, E., et al.; Pauletti, D. et al., Applications of a modified computer algorithm in determining potential antigenic determinants associated with AIDS virus glycoprotein. *Anal. Biochem.* 151: 540-546, 1985).

One potential use of F4 is thus to localize the peptide(s) of amino acids that are in the extracellular compartment of P-glycoprotein. In addition, the epitope recognized by McAb F4 has been identified from a very limited number of surgical specimens. The potential clinical application of F4 is thus implicated. It is noted that in 6 tissue specimens (1 sarcoma, 1 malignant lymphoma, 1 small carcinoma of the lung, 1 undifferential carcinoma of jugular nodes, and 2 adenocarcinomas of the lung) and in comparison with C219, F4 detected a single band at Mr 170–180,000, whereas C219 detected an extra band at Mr 63,000, in the sarcoma sample and both specimens of adenocarcinoma of the lung.

All of the above-cited references are incorporated herein by reference.

What is claimed is:

1. A monoclonal antibody, against soluble P-glycoprotein, designated F4.

2. A hybridoma cell line designated F4 which produces a monoclonal antibody against a soluble P-glycoprotein.

3. A method for detecting the presence of P-glycoprotein comprising reacting a specimen containing P-glycoprotein with the monoclonal antibody of claim 1 and detecting the reaction to show that P-glycoprotein is present.

4. The method of claim 3 wherein the reaction between the monoclonal antibody and P-glycoprotein is detected using a procedure selected from chemiluminescence, radioimmunoassay, immuno-fluorescence, colorometric analysis or spectrophotometry.

5. A method for detecting the presence of drug resistant carcinoma cells, in the absence of biopsy, comprising removing extracellular fluids from a patient for use as a specimen, and determining the presence of P-glycoprotein in the specimen in accordance with the method of claim 3, as an indicator of drug resistance.

6. The method of claim 5 wherein the extracellular fluid is ascites from an area around a tumor site.

* * * * *